United States Patent
Burkhardt et al.

(10) Patent No.: US 11,389,546 B2
(45) Date of Patent: Jul. 19, 2022

(54) HETEROLOGOUS UTR SEQUENCES FOR ENHANCED MRNA EXPRESSION

(71) Applicant: ModernaTX, Inc., Cambridge, MA (US)

(72) Inventors: David H. Burkhardt, Somerville, MA (US); Romesh R. Subramanian, Framingham, MA (US); Christian Cobaugh, Newton Highlands, MA (US)

(73) Assignee: ModernaTX, Inc., Cambridge, MA (US)

( * ) Notice: Subject to any disclaimer, the term of this patent is extended or adjusted under 35 U.S.C. 154(b) by 546 days.

(21) Appl. No.: 15/781,827

(22) PCT Filed: Dec. 9, 2016

(86) PCT No.: PCT/US2016/065796
§ 371 (c)(1),
(2) Date: Jun. 6, 2018

(87) PCT Pub. No.: WO2017/100551
PCT Pub. Date: Jun. 15, 2017

(65) Prior Publication Data
US 2018/0353618 A1 Dec. 13, 2018

Related U.S. Application Data

(60) Provisional application No. 62/265,233, filed on Dec. 9, 2015.

(51) Int. Cl.
| | | |
|---|---|---|
| *C12N 15/67* | (2006.01) | |
| *A61P 1/16* | (2006.01) | |
| *A61K 48/00* | (2006.01) | |
| *C12N 15/10* | (2006.01) | |
| *A61P 31/14* | (2006.01) | |
| *A61K 31/7115* | (2006.01) | |
| *A61K 31/712* | (2006.01) | |
| *A61K 31/7125* | (2006.01) | |
| *C12Q 1/68* | (2018.01) | |

(52) U.S. Cl.
CPC ........ *A61K 48/0058* (2013.01); *A61K 31/712* (2013.01); *A61K 31/7115* (2013.01); *A61K 31/7125* (2013.01); *A61K 48/0066* (2013.01); *A61P 1/16* (2018.01); *A61P 31/14* (2018.01); *C12N 15/1086* (2013.01); *C12N 15/67* (2013.01); *C12N 2840/00* (2013.01)

(58) Field of Classification Search
None
See application file for complete search history.

(56) References Cited

U.S. PATENT DOCUMENTS 8,278,036 B2  10/2012  Kariko et al.
8,835,108 B2   9/2014  Kariko et al.
2013/0156849 A1  6/2013  Fougerolles et al.
2014/0147454 A1*  5/2014  Chakraborty .......... A61K 39/00
424/185.1
2021/0317468 A1* 10/2021  Limphong ............. C12N 15/52

FOREIGN PATENT DOCUMENTS

WO   WO 2013/044008    3/2013
WO   WO 2014/081507    5/2014
WO   WO 2014/164253   10/2014
WO   WO 2017/100551    6/2015

OTHER PUBLICATIONS

Anderson et al., "Nucleoside modifications in RNA limit activation of 2'-5'-oligoadenylate synthetase and increase resistance to cleavage by RNase L," Nucleic Acids Res., 39:9329-38, 2011.
Database Accession No. BAM82145, "Human albumin DNA sequense, SEQ ID 160," (May 23, 2013).
Database Accession No. BC105803, "*Homo sapiens* fibrinogen alpha chain, mRNA (cDNA clone IMAGE:4711814), partial cds," (Oct. 2, 2005).
Database Accession No. BG485411, "602505289F1 NIH_MGC_77 *Homo sapiens* cDNA clone IMAGE:4618654 5', mRNA sequence," (Mar. 23, 2001).
Database Accession No. BP294073, "*Homo sapiens* cDNA clone: LVR00149, Sugano cDNA library, expressed in liver, 5'-EST," (Sep. 10, 2004).
Database Accession No. BX494172, "*Homo sapiens* mRNA; EST DKFZp779J221_rl (from clone DKFZp779J2211)," (May 9, 2003).
Database Accession No. DC621312, "*Macaca fascicularis* mRNA, clone: Q1vC-03193, 5' end, expressed in liver," (Feb. 22, 2008).
Database Accession No. DC628220, "*Macaca fascicularis* mRNA, clone: Q1vC-26291, 5' end, expressed in liver," (Feb. 22, 2008).
Database Accession No. HY029451, "*Homo sapiens* cDNA, clone:H04D101N21, expressed in male testis RIKEN full-legth enriched library, 5' end partial sequence," (May 20, 2012).
Database Accession No. M55658, "Human complement C3 protein mRNA, 5' flank," (May 6, 1992).
Emani et al., "RNA stability regulates differential expression of the metastasis protein, osteopontin, in hepatocellular cancer," Surgery, 143(6):803-812 (Jun. 2008).
Fritz et al., "RNA-binding protein RBMS3 is expressed in activated hepatic stellate cells and liver fibrosis and increases expression of transcription factor Prx1," Journal of Molecular Biology, 371(3):585-595 (Jul. 2007).
International Preliminary Report on Patentability in International Application No. PCT/US2016/065796, dated Jun. 21, 2018, 15 pages.
International Search Report and Written Opinion in International Application No. PCT/US2016/065796, dated May 9, 2017, 26 pages.
Invitation to Pay Additional Fees in International Application No. PCT/US2016/065796, dated Mar. 20, 2017, 12 pages.

(Continued)

*Primary Examiner* — Sean McGarry
(74) *Attorney, Agent, or Firm* — Fish & Richardson P.C.

(57) ABSTRACT mRNAs containing an exogenous open reading frame (ORF) flanked by a 5' untranslated region (UTR) and a 3' UTR is provided, wherein the 5' and 3' UTRs are derived from a naturally abundant mRNA in a tissue. Also provided are methods for identifying the 5' and 3' UTRs, and methods for making and using the mRNAs.

12 Claims, 7 Drawing Sheets
Specification includes a Sequence Listing.

(56) References Cited

OTHER PUBLICATIONS

Karikó et al., "Suppression of RNA recognition by Toll-like receptors: the impact of nucleoside modification and the evolutionary origin of RNA," Immunity, 23:165-75 (Aug. 2005).

Karikó et al., "Incorporation of pseudouridine into mRNA yields superior nonimmunogenic vector with increased translational capacity and biological stability," Mol., Ther., 16:1833-40, (Nov. 2008).

Kormann et al., "Expression of therapeutic proteins after delivery of chemically modified mRNA in mice," Nat. Biotechnol. 29:154-7, 2011.

Kreiter et al., "Intranodal vaccination with naked antigen-encoding RNA elicits potent prophylactic and therapeutic antitumoral immunity," Cancer Res., 70:9031-40, (Nov. 2010).

Mandal et al., "Reprogramming human fibroblasts to pluripotency using modified mRNA," Nature Protocols, 2013, 8:568-582.

Matsui et al., "Messenger RNA-based therapeutics for the treatment of apoptosis-associated diseases," Scientific Reports, 5:15810 (Oct. 2015).

Ramsköld et al., "An abundance of ubiquitously expressed genes revealed by tissue transcriptome sequence data.," PLOS Comput. Biol., 5:e1000598, 2009.

Schwanhäusser et al., "Global quantification of mammalian gene expression control," Nature, 473:337-42, 2011.

Tavernier et al., "mRNA as gene therapeutic: How to control protein expression," Journal of Controlled Release, 150(3):238-247 (Mar. 2011).

Thess et al., "Sequence-engineered mRNA Without Chemical Nucleoside Modifications Enables an Effective Protein Therapy in Large Animals," Mol. Ther., 23:1456-64, 2015.

Uchida et al., "491. Messenger RNA (mRNA)-Based Gene Therapy for Introducing Anti-Apoptotic Factor," Molecular Therapy, 23(Suppl. 1):S195 (May 2015).

Warren et al., "Highly efficient reprogramming to pluripotency and directed differentiation of human cells with synthetic modified mRNA," Cell Stem Cell, 7:618-30, 2010.

Zhao et al., "Multiple injections of electroporated autologous T cells expressing a chimeric antigen receptor mediate regression of human disseminated tumor," Cancer Res., 70:9053-61, 2010.

\* cited by examiner

HETEROLOGOUS UTR SEQUENCES FOR ENHANCED MRNA EXPRESSION

BACKGROUND

Messenger RNA (mRNA) is frequently used as a gene delivery molecule in the field of cancer immunotherapy and stem cell-based biomedical research as an alternative to plasmid DNA. As a direct source of gene products, mRNA has several advantages including a lack of requirement for nuclear entry, which poses a significant barrier to DNA delivery, especially in non-dividing cells. mRNA also has a negligible chance of integrating into the host genome, avoiding aberrant transcription and expression of oncogenes caused by insertional mutagenesis.

For a given gene, the untranslated gene regions (UTRs), including the 5' and 3' UTRs, are regions involved in the regulation of expression. The 5' UTR is a regulatory region of DNA situated at the 5' end of all protein coding sequence that is transcribed into mRNA but not translated into protein. 5' UTRs may contain various regulatory elements, e.g., 5' cap structure, G-quadruplex structure (G4), stem-loop structure, and internal ribosome entry sites (IRES), which play a major role in the control of translation initiation. The 3' UTR, situated downstream of the protein coding sequence, has been found to be involved in numerous regulatory processes including transcript cleavage, stability and polyadenylation, translation, and mRNA localization. The 3' UTR serves as a binding site for numerous regulatory proteins and small non-coding RNAs, e.g., microRNAs.

Current mRNA therapies typically rely on native or standard UTR sequences that are often not tissue-specific and/or give low levels of protein expression. There is a need to identify novel UTRs that can stabilize therapeutic mRNA and increase protein synthesis in a tissue-specific manner.

SUMMARY

The present disclosure relates to methods of improving expression from an mRNA in a tissue (e.g., liver, or cells in vitro, such as stem cells, hepatocytes or lymphocytes), and heterologous untranslated region (UTR) sequences for enhancing protein synthesis from therapeutic mRNAs (including those UTRs that act in a tissue-specific manner), methods of identifying the same, and methods of using the same as therapeutic agents. Sequence elements provided herein include, for example, UTRs derived from mRNAs that are naturally abundant in a specific tissue (e.g., liver), to which the therapeutic mRNA's expression is targeted.

UTR sequences of the present disclosure may, for example, increase protein synthesis by increasing both the time that the mRNA remains in translating polysomes (message stability) and/or the rate at which ribosomes initiate translation on the message (message translation efficiency). Thus, UTR sequences of the present disclosure lead to prolonged protein synthesis, enabling successful treatment of conditions that require continuous protein expression in a tissue-specific manner.

Described herein are mRNAs comprising an exogenous open reading frame (ORF) flanked by a 5' UTR and a 3' UTR, wherein the 5' UTR and the 3' UTR are derived from a naturally abundant mRNA in a tissue. The tissue may be, for example, liver, a stem cell or lymphoid tissue. The lymphoid tissue may be, for example, a lymphocyte (e.g., a B-lymphocyte, a helper T-lymphocyte, a cytotoxic T-lymphocyte, a regulatory T-lymphocyte, or a natural killer cell), a macrophage, a monocyte, a dendritic cell, a neutrophil, an eosinophil or a reticulocyte. The naturally abundant mRNA may have, for example, a tissue half-life of at least about 9 hours, or from about 5 to about 60 hours. The naturally abundant mRNA may be, for example, transcribed from HP, FGB, HPR, ALB, C3, FGA, SERPINA1 or SERPINA3 gene. The 5' UTR may have, for example, the nucleotide sequence of SEQ ID NOS: 1-6, 9 or 10. The exogenous ORF may be, for example, a reporter gene or a therapeutic gene. The therapeutic gene may be, for example, interferon alpha, TNF-related apoptosis-inducing ligand, vascular adhesion protein 1, or hepatocyte growth factor. The mRNA may include, for example, at least one non-natural or modified nucleotide. The at least one non-natural or modified nucleotide may include, for example, at least one backbone modification, sugar modification or base modification. The at least one non-natural or modified nucleotide may include, for example, at least one base modification. The at least one base modification, for example, may be selected from the group consisting of 2-amino-6-chloropurine riboside 5'-triphosphate, 2-aminoadenosine 5'-triphosphate, 2-thiocytidine 5'-triphosphate, 2-thiouridine 5'-triphosphate, 4-thiouridine 5'-triphosphate, 5-aminoallylcytidine 5'-triphosphate, 5-aminoallyluridine 5'-triphosphate, 5-bromocytidine 5'-triphosphate, 5-bromouridine 5'-triphosphate, 5-iodocytidine 5'-triphosphate, 5-iodouridine 5'-triphosphate, 5-methylcytidine 5'-triphosphate, 5-methyluridine 5'-triphosphate, 6-azacytidine 5'-triphosphate, 6-azauridine 5'-triphosphate, 6-chloropurine riboside 5'-triphosphate, 7-deazaadenosine 5'-triphosphate, 7-deazaguanosine 5'-triphosphate, 8-azaadenosine 5'-triphosphate, 8-azidoadenosine 5'-triphosphate, benzimidazole riboside 5'-triphosphate, N1-methyladenosine 5'-triphosphate, N1-methylguanosine 5'-triphosphate, N6-methyladenosine 5'-triphosphate, $O^6$-methylguanosine 5'-triphosphate, $N^1$-methyl-pseudouridine 5'-triphosphate, puromycin 5'-triphosphate and xanthosine 5'-triphosphate. The at least one non-natural or modified nucleotide may, for example, be $N^1$-methyl-pseudouridine 5'-triphosphate.

Described herein are methods of identifying a 5' UTR and a 3' UTR for increasing protein synthesis in a desired tissue or a cell derived from the desired tissue, comprising a) isolating a plurality of 5' UTRs and a plurality of 3' UTRs from mRNAs that are naturally abundant in the desired tissue; b) generating a library of test constructs, each comprising a reporter ORF flanked by one of the plurality of 5' UTRs and/or one of the plurality of 3' UTRs; c) providing a reference construct comprising the reporter ORF flanked by reference 5' and 3' UTRs; d) expressing each of the test constructs and the reference construct in the tissue; e) measuring the protein expression of the reporter ORF from the each of the test constructs and the reference construct; f) selecting at least one test construct having a higher protein expression from the reporter ORF than the reference construct; and g) identifying the 5' UTR and the 3' UTR of the selected test construct. In a particular embodiment, the desired tissue is liver. In a particular embodiment, an mRNA comprising an identified 5' UTR or 3' UTR has a tissue half-life of at least 4 hours. In a particular embodiment, the reporter ORF is eGFP, adiponectin or Factor VII.

Described herein are methods treating a liver condition, comprising administering to a subject in need thereof the mRNA as described herein. In a particular embodiment, the liver condition is selected from the group consisting of: acute hepatitis, chronic hepatitis, liver cirrhosis, cirrhosis, fatty liver, liver cancer, glycogen storage disease, progressive familial intrahepatic cholestasis 1 (PFIC1), progressive familial intrahepatic cholestasis 2 (PFIC2), progressive familial intrahepatic cholestasis 3 (PFIC3), adenylosuccinate lyase deficiency (ASLD), citrullinemia, arginase-1 deficiency, primary hyperoxaluria type 1 (PH1), ornithine transcarbamylase deficiency (OTCD), homocystinuria, pheylketonuria, glycogen storage disease type IV (GSDIV), galactose-1-phosphate uridylyltransferase deficiency (type I (GALTI), type II (GALTII) or type 3 (GALTIII)), long chain 3-hydroxyacyl-CoA dehydrogenase deficiency (LCHADD), 3-methylcrotonyl-CoA carboxylase deficiency (MCCC1 deficiency), methylmalonic aciduria (MMA), MMA and homocystinuria type C (MMACHC), thrombotic thrombocytopenic purpura (TTP), hyperornithinemia-hyperammonemia-homocitrullinuria syndrome (HHH), complement component 2 deficiency (C2D), F2, protein S deficiency (caused by allelic variants of PROS1), alpha-1 antitrypsin deficiency (A1AT), glutaric academia 1 (GA-1), glutaric academia 2 (GA-2), cystinosis (CTNS), tyrosinemia, tyrosinemia type 3 (cause by allelic variants of HPD), D-bifunctional protein deficiency (DBP), Fanconi-Bickel syndrome (FBS), pseudoxanthoma elasticum (PXE), primary biliary cirrhosis, Pompe disease, glycerol kinase deficiency (GKD), proprionic acidemia (PA) and Crigler-Najjar syndrome (CN1). In a particular embodiment, the liver condition is hepatitis C. In a particular embodiment, the therapeutic gene is selected from the group consisting of: interferon alpha, TNF-related apoptosis-inducing ligand, vascular adhesion protein 1, hepatocyte growth factor, G6PC, ABCB11, ABCB4, ASL1, ASS, Arg1, AGXT, OTC, CBS, PAH, GBE, GALE, HADH, MCCC1, MMA, ADAMTS13, SLC25A15, C2, F2, PROS1, SERPINA1, GALT1, ETFA, GCDH, CTNS, FAH, TAT, HPD, HSD17b4, SLC2A2, GALC, ABCC6, AHSG, PDC-E2, GAA, ATP8B1, MMACHC, GK, PCCA, PCCB and UGT1A1.

Described herein are methods of improving expression of a protein in a desired cell or desired tissue, comprising providing an mRNA to said cell or tissue, wherein the mRNA comprises an open reading frame (ORF) that encodes said protein, flanked by a heterologous 5' untranslated region (UTR) and/or a heterologous 3' UTR, wherein the 5' UTR and/or the 3' UTR are derived from an mRNA that is naturally abundant mRNA in the desired tissue or tissues from which the desired cell was derived. In a particular embodiment, the mRNA comprises at least one modified or non-naturally occurring nucleotide. In a particular embodiment, the at least one modified or non-naturally occurring nucleotide comprises at least one backbone modification, sugar modification or base modification. In a particular embodiment, the at least one modified or non-naturally occurring nucleotide comprises at least one base modification. In a particular embodiment, the at least one base modification is selected from the group consisting of: 2-amino-6-chloropurine riboside 5' triphosphate, 2-aminoadenosine 5' triphosphate, 2-thiocytidine 5' triphosphate, 2-thiouridine 5' triphosphate, 4-thiouridine 5' triphosphate, 5-aminoallylcytidine 5' triphosphate, 5-aminoallyluridine 5' triphosphate, 5-bromocytidine 5' triphosphate, 5-bromouridine 5' triphosphate, 5-iodocytidine 5' triphosphate, 5-iodouridine 5' triphosphate, 5-methylcytidine 5' triphosphate, 5-methyluridine 5' triphosphate, 6-azacytidine 5' triphosphate, 6-azauridine 5' triphosphate, 6-chloropurine riboside 5'-triphosphate, 7-deazaadenosine 5' triphosphate, 7-deazaguanosine 5' triphosphate, 8-azaadenosine 5' triphosphate, 8-azidoadenosine 5' triphosphate, benzimidazole riboside 5' triphosphate, $N^1$-methyladenosine 5' triphosphate, $N^1$-methylguanosine 5' triphosphate, $N^6$-methyladenosine 5' triphosphate, $O^6$-methylguanosine 5' triphosphate, $N^1$-methyl-pseudouridine 5' triphosphate, puromycin 5'-triphosphate and xanthosine 5' triphosphate. In a particular embodiment, the at least one modified or non-naturally occurring nucleotide is $N^1$-methyl-pseudouridine 5-triphosphate. In a particular embodiment, the tissue is liver. In a particular embodiment, the mRNA has a half-life of at least 40 hours. In a particular embodiment, the heterologous 5' UTR and/or the heterologous 3' UTR is derived from a gene selected from the group consisting of: HP, FGB, HPR, ALB, C3, FGA, Col1A, Col6A, SERPINA1 and SERPINA3. In a particular embodiment, the 5' UTR comprises a nucleotide sequence selected from the group consisting of: SEQ ID NOS: 1-6, 9 and 10. In a particular embodiment, the ORF is a reporter gene or a therapeutic gene of interest. In a particular embodiment, the therapeutic gene is selected from the group consisting of: interferon alpha, TNF-related apoptosis-inducing ligand, vascular adhesion protein 1, hepatocyte growth factor, G6PC, ABCB11, ABCB4, ASL1, ASS, Arg1, AGXT, OTC, CBS, PAH, GBE, GALE, HADH, MCCC1, MMA, ADAMTS13, SLC25A15, C2, F2, PROS1, SERPINA1, GALT1, ETFA, GCDH, CTNS, FAH, TAT, HPD, HSD17b4, SLC2A2, GALC, ABCC6, AHSG, PDC-E2, GAA, ATP8B1, MMACHC, GK, PCCA, PCCB and UGT1A1.

DETAILED DESCRIPTION

Disclosed herein are methods of improving expression from an mRNA, e.g., in a tissue-specific manner (e.g., liver, or cells in vitro, such as stem cells or lymphocytes), untranslated region (UTR) sequences for enhancing protein synthesis from mRNAs of interest, such as, for example, therapeutic mRNAs, methods of identifying the same, and methods of using the same as therapeutic agents. UTRs are described, for example, to increase translation and mRNA stability. Globin 5'- and 3'-UTRs, for example, were used to improve translation and mRNA stability of heterologous mRNA and of in vitro transcribed mRNA for immune therapy (Zhao, Y et al., *Cancer Res.*, 70:9053-61, 2010; Kreiter, S. et al., *Cancer Res.*, 70:9031-40, 2010). The 5'-UTR of tobacco etch virus (TEV) was also shown to enhance translation of in vitro transcribed mRNA in mammalian cells and was used to express erythropoietin in mice.

It is to be understood that the disclosure is not limited to the particular embodiments of the present disclosure described below, as variations of the particular embodiments may be made and still fall within the scope of the appended claims. It is also to be understood that the terminology employed is for the purpose of describing particular embodiments, and is not intended to be limiting.

As used herein, the singular forms "a," "an" and "the" include plural reference unless the context clearly dictates otherwise. Unless defined otherwise, all technical and scientific terms used herein have the same meaning as commonly understood to one of ordinary skill in the art to which this disclosure belongs.

The term "functionally linked" or "operably linked" means in this context the sequential and function arrangement between a 5' UTR, open reading frame (ORF), and 3' UTR according to the present disclosure, wherein at least the 5' UTR modulates translation of said ORF.

The number of molecules of mRNA that can be delivered in a single therapeutic dose is limited by the toxicity of the delivery vehicle. For many diseases of interest, a high level of protein synthesis is required from each dose of mRNA to achieve a therapeutic effect. In some cases, currently available technology is unable to safely produce this high level of synthesis. Thus, achieving a therapeutic effect requires reducing the dose volume.

Disclosed herein are compositions and methods for increasing protein synthesis by increasing both the time that the mRNA remains in translating polysomes (message stability) and the rate at which ribosomes initiate translation on the message (message translation efficiency).

RNA is notoriously unstable. Rapid degradation of mRNA presents a major challenge to current therapeutic paradigms. Chronic mRNA dosing may be required to produce enough protein activity to adequately address the condition being treated. If a therapeutic mRNA is rapidly degraded following delivery, the result will be only a brief pulse of protein production. An extremely frequent dosing schedule would be necessary to achieve continuous protein expression from this rapidly degraded mRNA. But such a schedule would pose significant toxicity, compliance and efficacy challenges that may limit therapeutic efficacy. Reducing dose frequency, therefore, is desirable for improving therapeutic efficacy.

Figure 1:
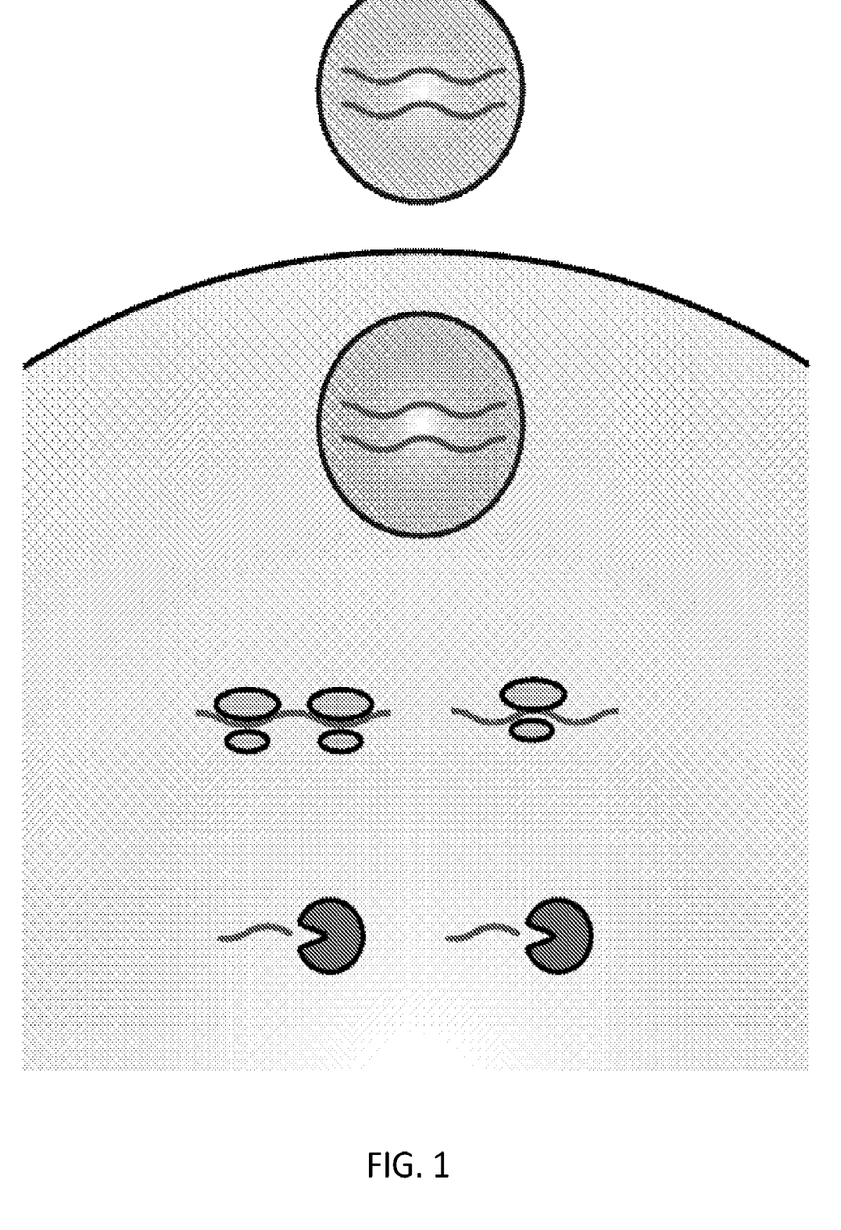
FIG. 1 shows degradation process of formulated mRNA after delivery into a cell. After formulated mRNA is delivered and endocytosed into a cell, ribosomes bind to mRNA to form polysomal mRNA for active translation, followed by mRNA degradation.
Figure 2:
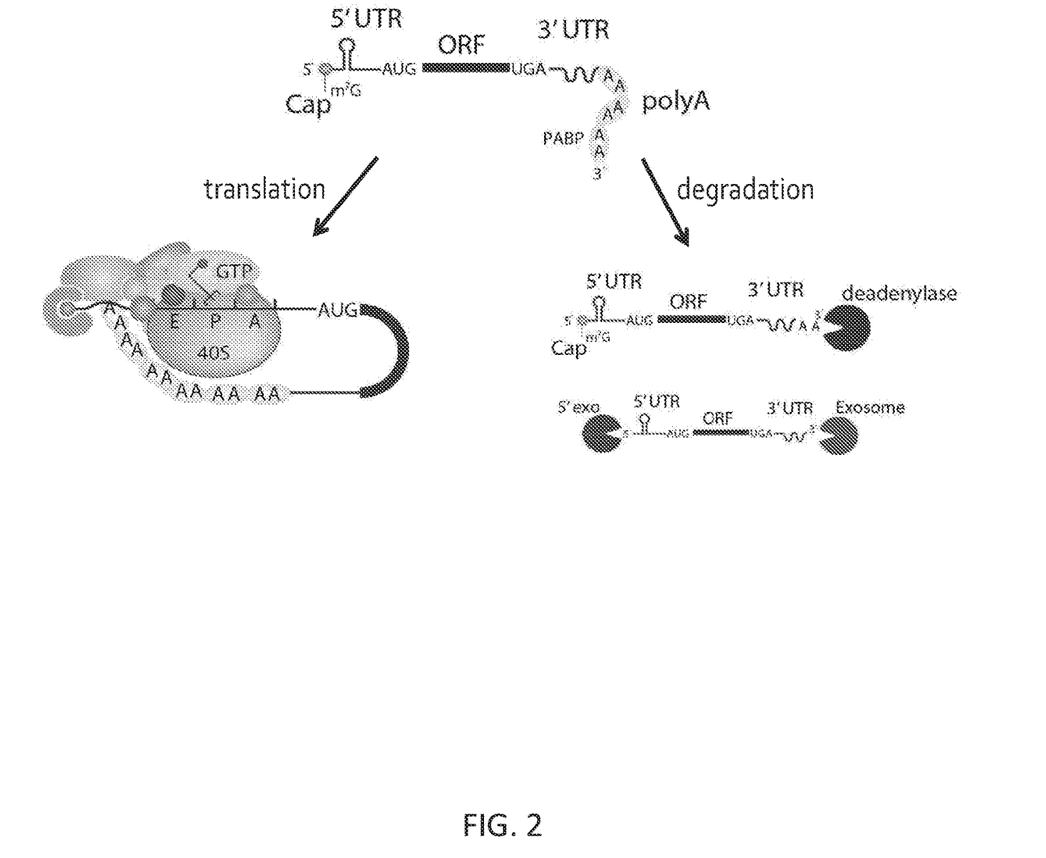
FIG. 2 shows major paths for mRNA degradation. Nearly all major mRNA decay pathways characterized in eukaryotes are initiated by deadenylation by deadenylases. Deadenylation primarily leads to decapping at the 5' end with subsequent 5' to 3' exonucleolytic digestion of the RNA body by 5' exonucleases (5' exo). Alternatively, when the 5' to 3' decay pathway is compromised, after deadenylation, the mRNA body can be degraded from the 3' end by a large complex called an exosome.
Figure 3:
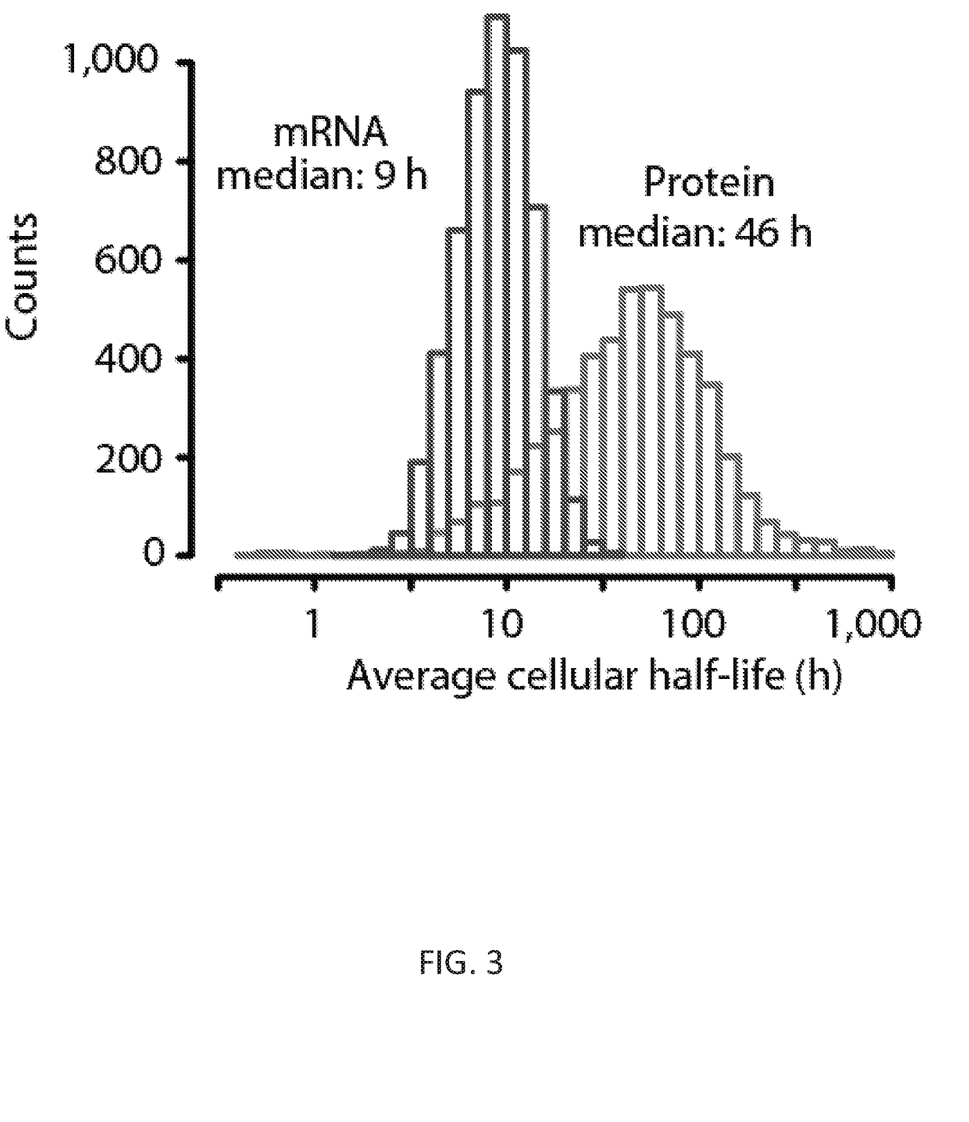
FIG. 3 shows a wide range of stabilities of endogenous mRNAs. By increasing the upper limit of mRNA half-life, the quantity of protein delivered may be dramatically increased.

Endogenous mRNAs show a wide range of stabilities. The most stable endogenous mRNAs have half-lives of from 40 to 60 hours (Schwanhausser, B. et al., *Nature*, 473:337-42, 2011), as indicated by the arrow in FIG. 3. By increasing the upper limit of mRNA half-life, the quantity of protein delivered may be dramatically increased.

RNA stability may also be increased in a tissue-specific manner. Every tissue comprises a set of core genes that are active in for each tissue (Ramsköld, D. et al., *PLOS Comput. Biol.*, 5:e1000598, 2009). The tissue-specific mRNAs from such core genes accounts for the majority of all RNA molecules (transcriptome) in each tissue. For example, the ten most abundantly expressed genes in mouse liver represent 25% of all mRNAs in that tissue. These observations suggest that enhanced RNA stability contributes to abundance of these mRNAs in liver.

As noted above, UTR sequences can modulate mRNA stability through a variety of mechanisms, including mRNA binding proteins, miRNA, and secondary structures, which directly inhibit nucleolytic degradation. Molecular engineering has, in some instances, led to a 100× improvement in protein synthesis, a major component of which is altering UTR sequences (Thess, A. et al., *Mol. Ther.*, 23:1456-64, 2015).

The present disclosure improves upon current technology to enhance expression from an mRNA construct, e.g., by decreasing the rate of mRNA degradation to increase both the duration and the magnitude of protein synthesis produced from an mRNA dose, especially in a tissue-specific manner. The mRNA described herein can contain, for example, a hybrid sequence, which may comprise an open reading frame (ORF) for a target polypeptide of interest coupled (upstream of the target of interest) to a heterologous, e.g., a tissue-specific, UTR derived from another naturally occurring or engineered gene (e.g., a human gene or an engineered UTR from a human gene). The mRNA construct(s) described herein can optionally comprise, for example, a poly-adenosine region (poly-A tail) downstream of the target of the ORF.

The mRNA(s) described herein can comprise naturally occurring ribonucleosides or chemically modified ribonucleosides, i.e., modified mRNAs (modRNAs). modRNAs can be prepared as described in, for example, U.S. Pat. No. 8,278,036 (incorporated herein by reference), to include one or more pseudouridine residues, for example. Uridine and cytidine, for example, can be replaced with 2-thiouridine and/or 5-methylcytidine to increase stability of the mRNA.

The described mRNA can comprise at least one structural or chemical modification. The nucleoside that is modified in the mRNA, for example, can be a uridine (U), a cytidine (C), an adenine (A), or guanine (G). The modified nucleoside can be, for example, $m^5C$ (5-methylcytidine), $m^6A$ ($N^6$-methyladenosine), $s^2U$ (2-thiouridien), ψ (pseudouridine) or Um (2-O-methyluridine). Some exemplary chemical modifications of nucleosides in the mRNA molecule further include, for example, pyridine-4-one ribonucleoside, 5-aza-uridine, 2-thio-5-aza uridine, 2-thiouridine, 4-thio pseudouridine, 2-thio pseudouridine, 5-hydroxyuridine, 3-methyluridine, 5-carboxymethyl uridine, 1-carboxymethyl pseudouridine, 5-propynyl uridine, 1-propynyl pseudouridine, 5-taurinomethyluridine, 1-taurinomethyl pseudouridine, 5-taurinomethyl-2-thio uridine, 1-taurinomethyl-4-thio uridine, 5-methyl uridine, 1-methyl pseudouridine, 4-thio-1-methyl pseudouridine, 2-thio-1-methyl pseudouridine, 1-methyl-1-deaza pseudouridine, 2-thio-1-methyl-1-deaza pseudouridine, dihydrouridine, dihydropseudouridine, 2-thio dihydrouridine, 2-thio dihydropseudouridine, 2-methoxyuridine, 2-methoxy-4-thio uridine, 4-methoxy pseudouridine, 4-methoxy-2-thio pseudouridine, 5-aza cytidine, pseudoisocytidine, 3-methyl cytidine, N4-acetylcytidine, 5-formylcytidine, N4-methylcytidine, 5-hydroxymethylcytidine, 1-methyl pseudoisocytidine, pyrrolo-cytidine, pyrrolo-pseudoisocytidine, 2-thio cytidine, 2-thio-5-methyl cytidine, 4-thio pseudoisocytidine, 4-thio-1-methyl pseudoisocytidine, 4-thio-1-methyl-1-deaza pseudoisocytidine, 1-methyl-1-deaza pseudoisocytidine, zebularine, 5-aza zebularine, 5-methyl zebularine, 5-aza-2-thio zebularine, 2-thio zebularine, 2-methoxy cytidine, 2-methoxy-5-methyl cytidine, 4-methoxy pseudoisocytidine, 4-methoxy-1-methyl pseudoisocytidine, 2-aminopurine, 2,6-diaminopurine, 7-deaza adenine, 7-deaza-8-aza adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, $N^6$-methyladenosine, $N^6$-isopentenyladenosine, $N^6$-(cis-hydroxyisopentenyl) adenosine, 2-methylthio-$N^6$-(cis-hydroxyisopentenyl) adenosine, $N^6$-glycinylcarbamoyladenosine, $N^6$-threonylcarbamoyladenosine, 2-methylthio-$N^6$-threonyl carbamoyladenosine, $N^6,N^6$-dimethyladenosine, 7-methyladenine, 2-methylthio adenine, 2-methoxy adenine, inosine, 1-methyl inosine, wyosine, wybutosine, 7-deaza guanosine, 7-deaza-8-aza guanosine, 6-thio guanosine, 6-thio-7-deaza guanosine, 6-thio-7-deaza-8-aza guanosine, 7-methyl guanosine, 6-thio-7-methyl guanosine, 7-methylinosine, 6-methoxy guanosine, 1-methylguanosine, $N^2$-methylguanosine, $N^2,N^2$-dimethylguanosine, 8-oxo guanosine, 7-methyl-8-oxo guanosine, 1-methyl-6-thio guanosine, $N^2$-methyl-6-thio guanosine, and $N^2,N^2$-dimethyl-6-thio guanosine. In another embodiment, the modifications are independently selected from the group consisting of 5-methylcytosine, pseudouridine and 1-methylpseudouridine.

In some embodiments, the modified nucleobase in the mRNA molecule is a modified uracil including, for example, pseudouridine (ψ), pyridine-4-one ribonucleoside, 5-aza uridine, 6-aza uridine, 2-thio-5-aza uridine, 2-thio uridine (s2U), 4-thio uridine (s4U), 4-thio pseudouridine, 2-thio pseudouridine, 5-hydroxy uridine (ho$^5$U), 5-aminoallyl uridine, 5-halo uridine (e.g., 5-iodom uridine or 5-bromo uridine), 3-methyl uridine (m$^3$U), 5-methoxy uridine (mo$^5$U), uridine 5-oxyacetic acid (cmo$^5$U), uridine 5-oxyacetic acid methyl ester (mcmo$^5$U), 5-carboxymethyl uridine (cm$^5$U), 1-carboxymethyl pseudouridine, 5-carboxyhydroxymethyl uridine (chm$^5$U), 5-carboxyhydroxym ethyl uridine methyl ester (mchm$^5$U), 5-methoxycarbonylmethyl uridine (mcm$^5$U), 5-methoxycarbonylmethyl-2-thio uridine (mcm$^5$s2U), 5-aminomethyl-2-thio uridine (nm$^5$s2U), 5-methylaminomethyl uridine (mnm$^5$U), 5-methylaminomethyl-2-thio uridine (mnm$^5$s2U), 5-methylaminomethyl-2-seleno uridine (mnm$^5$se$^2$U), 5-carbamoylmethyl uridine (ncm$^5$U), 5-carboxymethylaminomethyl uridine (cmnm$^5$U), 5-carboxymethylaminomethyl-2-thio uridine (cmnm$^5$s2U), 5-propynyl uridine, 1-propynyl pseudouridine, 5-taurinomethyl uridine (τcm$^5$U), 1-taurinomethyl pseudouridine, 5-taurinomethyl-2-thio uridine (τM$^5$s2U), 1-taurinomethyl-4-thio pseudouridine, 5-methyl uridine (m$^5$U, e.g., having the nucleobase deoxythymine), 1-methyl pseudouridine (m$^1$ψ), 5-methyl-2-thio uridine (m$^5$s2U), 1-methyl-4-thio pseudouridine (m$_1$s$^4$ψ), 4-thio-1-methyl pseudouridine, 3-methyl pseudouridine (m$^3$ψ), 2-thio-1-methyl pseudouridine, 1-methyl-1-deaza pseudouridine, 2-thio-1-methyl-1-deaza pseudouridine, dihydrouridine (D), dihydropseudouridine, 5,6-dihydrouridine, 5-methyl dihydrouridine (m$^5$D), 2-thio dihydrouridine, 2-thio dihydropseudouridine, 2-methoxy uridine, 2-methoxy-4-thio uridine, 4-methoxy pseudouridine, 4-methoxy-2-thio pseudouridine, $N^1$-methyl pseudouridine, 3-(3-amino-3-carboxypropyl) uridine (acp$^3$U), 1-methyl-3-(3-amino-3-carboxypropyl) pseudouridine (acp$^3$ψ), 5-(isopentenylaminomethyl) uridine (inm$^5$U), 5-(isopentenylaminomethyl)-2-thio uridine (inm$^5$s2U), .alpha-thio uridine, 2'-O-methyl uridine (Um), 5,2'-O-dimethyl uridine (m$^5$Um), 2'-O-methyl pseudouridine (ψm), 2-thio-2'-O-methyl uridine (s2Um), 5-methoxycarbonylmethyl-2'-O-methyl uridine (mcm$^5$Um), 5-carbamoylmethyl-2'-O-methyl uridine (ncm$^5$Um), 5-carboxymethylaminomethyl-2'-O-methyl uridine (cmnm$^5$Um), 3,2'-O-dimethyl uridine (m$^3$Um), 5-(isopentenylaminomethyl)-2'-O-methyl uridine (inm$^5$Um), 1-thio uridine, deoxythymidine, 2'-F-ara uridine, 2'-F uridine, 2'-OH-ara uridine, 5-(2-carbomethoxyvinyl) uridine, and 5-[3-(1-E-propenylamino) uridine.

In some embodiments, the modified nucleobase is a modified cytosine including, for example, 5-aza cytidine, 6-aza cytidine, pseudoisocytidine, 3-methyl cytidine (m$^3$C), $N^4$-acetyl cytidine (act), 5-formyl cytidine (f$^5$C), $N^4$-methyl cytidine (m$^4$C), 5-methyl cytidine (m$^5$C), 5-halo cytidine (e.g., 5-iodo cytidine), 5-hydroxymethyl cytidine (hm$^5$C), 1-methyl pseudoisocytidine, pyrrolo-cytidine, pyrrolo-pseudoisocytidine, 2-thio cytidine (s2C), 2-thio-5-methyl cytidine, 4-thio pseudoisocytidine, 4-thio-1-methyl pseudoisocytidine, 4-thio-1-methyl-1-deaza pseudoisocytidine, 1-methyl-1-deaza pseudoisocytidine, zebularine, 5-aza zebularine, 5-methyl zebularine, 5-aza-2-thio zebularine, 2-thio zebularine, 2-methoxy cytidine, 2-methoxy-5-methyl cytidine, 4-methoxy pseudoisocytidine, 4-methoxy-1-methyl pseudoisocytidine, lysidine (k$^2$C), alpha-thio cytidine, 2'-O-methyl cytidine (Cm), 5,2'-O-dimethyl cytidine (m$^5$Cm), $N^4$-acetyl-2'-O-methyl cytidine (ac$^4$Cm), $N^4$,2'-O-dimethyl cytidine (m$^4$Cm), 5-formyl-2'-O-methyl cytidine (f$^5$Cm), $N^4,N^4$,2'-O-trimethyl cytidine (m$^4_2$Cm), 1-thio cytidine, 2'-F-ara cytidine, 2'-F cytidine, and 2'-OH-ara cytidine.

In some embodiments, the modified nucleobase is a modified adenine including, for example, 2-amino purine, 2,6-diamino purine, 2-amino-6-halo purine (e.g., 2-amino-6-chloro purine), 6-halo purine (e.g., 6-chloro purine), 2-amino-6-methyl purine, 8-azido adenosine, 7-deaza adenine, 7-deaza-8-aza adenine, 7-deaza-2-amino purine, 7-deaza-8-aza-2-amino purine, 7-deaza-2,6-diamino purine, 7-deaza-8-aza-2,6-diamino purine, 1-methyl adenosine (m$^1$A), 2-methyl adenine (m$^2$A), $N^6$-methyl adenosine (m$^6$A), 2-methylthio-$N^6$-methyl adenosine (ms$^2$m$^6$A), $N^6$-isopentenyl adenosine (i$^6$A), 2-methylthio-$N^6$-isopentenyl adenosine (ms$^2$i$^6$A), $N^6$-(cis-hydroxyisopentenyl) adenosine (io$^6$A), 2-methylthio-$N^6$-(cis-hydroxyisopentenyl) adenosine (ms$^2$io$^6$A), $N^6$-glycinylcarbamoyl adenosine (g$^6$A), $N^6$-threonylcarbamoyl adenosine (t$^6$A), $N^6$-methyl-$N^6$-threonylcarbamoyl adenosine (m$^6$t$^6$A), 2-methylthio-$N^6$-threonylcarbamoyl adenosine (ms$^2$g$^6$A), $N^6,N^6$-dimethyl adenosine (m$^6_2$A), $N^6$-hydroxynorvalylcarbamoyl adenosine (hn$^6$A), 2-methylthio-$N^6$-hydroxynorvalylcarbamoyl adenosine (ms$^2$hn$^6$A), $N^6$-acetyl adenosine (ac$^6$A), 7-methyl adenine, 2-methylthio adenine, 2-methoxy adenine, alpha-thio adenosine, 2'-O-methyl adenosine (Am), $N^6$,2'-O-dimethyl adenosine (m$^6$Am) $N^6,N^6$,2'-O-trimethyl adenosine (m$^6_2$Am), 1,2'-O-dimethyl adenosine (m$^1$Am), 2'-O-ribosyl adenosine (phosphate) (Ar(p)), 2-amino-$N^6$-methyl purine, 1-thio adenosine, 8-azido adenosine, 2'-F-ara adenosine, 2'-F adenosine, 2'-OH-ara adenosine, and $N^6$-(19-amino-pentaoxanonadecyl) adenosine.

In some embodiments, the modified nucleobase is a modified guanine including, for example, inosine (I), 1-methyl inosine (m¹I), wyosine (imG), methylwyosine (mimG), 4-demethyl wyosine (imG-14), isowyosine (imG2), wybutosine (yW), peroxywybutosine (o₂yW), hydroxywybutosine (OHyW), undermodified hydroxywybutosine (OHyWy), 7-deaza guanosine, queuosine (Q), epoxyqueuosine (oQ), galactosyl queuosine (galQ), mannosyl queuosine (manQ), 7-cyano-7-deaza guanosine (preQ₀), 7-aminomethyl-7-deaza guanosine (preQ₁), archaeosine (G⁺), 7-deaza-8-aza guanosine, 6-thio guanosine, 6-thio-7-deaza guanosine, 6-thio-7-deaza-8-aza guanosine, 7-methyl guanosine (m⁷G), 6-thio-7-methyl guanosine, 7-methyl inosine, 6-methoxy guanosine, 1-methyl guanosine (m¹G), N²-methyl-guanosine (m²G), N²,N²-dimethyl guanosine (m²₂G), N²,⁷-dimethyl guanosine (m²,⁷G), N²,N²,⁷-dimethyl guanosine (m²,²,⁷G), 8-oxo guanosine, 7-methyl-8-oxo guanosine, 1-methio guanosine, N²-methyl-6-thio guanosine, N²,N²-dimethyl-6-thio guanosine, alpha-thio guanosine, 2'-O-methyl guanosine (Gm), N²-methyl-2'-O-methyl guanosine (m²Gm), N²,N²-dimethyl-2'-O-methyl guanosine (m²₂Gm), 1-methyl-2'-O-methyl guanosine (m¹Gm), N²,⁷-dimethyl-2'-O-methyl guanosine (m²,⁷Gm), 2'-O-methyl inosine (Im), 1,2'-O-dimethyl inosine (m¹Im), 2'-O-ribosyl guanosine (phosphate) (Gr(p)), 1-thio guanosine, O⁶-methyl guanosine, 2'-F-ara guanosine, and 2'-F guanosine.

The nucleobase of the nucleotide can be independently selected from a purine, a pyrimidine, a purine or pyrimidine analog. For example, the nucleobase can each be independently selected from adenine, cytosine, guanine, uracil or hypoxanthine. The nucleobase can also include, for example, naturally occurring and synthetic derivatives of a base, including, but not limited to, pyrazolo[3,4-d]pyrimidines, 5-methylcytosine (5-me-C), 5-hydroxymethyl cytosine, xanthine, hypoxanthine, 2-amino adenine, 6-methyl and other alkyl derivatives of adenine and guanine, 2-propyl and other alkyl derivatives of adenine and guanine, 2-thio uracil, 2-thio thymine and 2-thio cytosine, 5-propynyl uracil and cytosine, 6-azo uracil, cytosine and thymine, pseudouracil, 4-thio uracil, 8-halo (e.g., 8-bromo), 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methyl guanine and 7-methyl adenine, 8-aza guanine and 8-aza adenine, deaza guanine, 7-deaza guanine, 3-deaza guanine, deaza adenine, 7-deaza adenine, 3-deaza adenine, pyrazolo[3,4-d] pyrimidine, imidazo[1,5-a]1,3,5 triazinones, 9-deaza purines, imidazo[4,5-d]pyrazines, thiazolo[4,5-d]pyrimidines, pyrazine-2-ones, 1,2,4-triazine, pyridazine; and 1,3,5-triazine. When the nucleotides are depicted using the shorthand A, G, C, T or U, each letter refers to the representative base and/or derivatives thereof, e.g., A includes adenine or adenine analogs, e.g., 7-deaza adenine).

Other modifications include, for example, those in U.S. Pat. No. 8,835,108; U.S. Patent Application Publication No. 20130156849; Tavernier, G. et al., *J. Control. Release*, 150:238-47, 2011; Anderson, B. et al., *Nucleic Acids Res.*, 39:9329-38, 2011; Kormann, M. et al., *Nat. Biotechnol.*, 29:154-7, 2011; Karikó, K. et al., *Mol. Ther.*, 16:1833-40, 2008; Karikó, K. et al., *Immunity*, 23:165-75, 2005; and Warren, L. et al., *Cell Stem Cell*, 7:618-30, 2010; the entire contents of each of which is incorporated herein by reference. The modRNAs can be prepared, for example, by incorporation of base-modified nucleotides, such as N¹-methyl-pseudouridine 5'-triphosphate, the chemical structure of which is shown below.

Described herein are UTRs derived from, for example, human genes that are naturally abundant and well-translated in the tissue being targeted. Such UTRs may be used to determine whether altering the UTRs extends mRNA half-life, thereby increasing protein production from mRNAs, e.g., modRNAs.

Described herein are libraries of constructs with UTRs, which may be screened to identify candidate UTRs that specifically increase mRNA stability in target tissues, such as liver, or cells in vitro, such as stem cells or lymphocytes.

Figure 4:
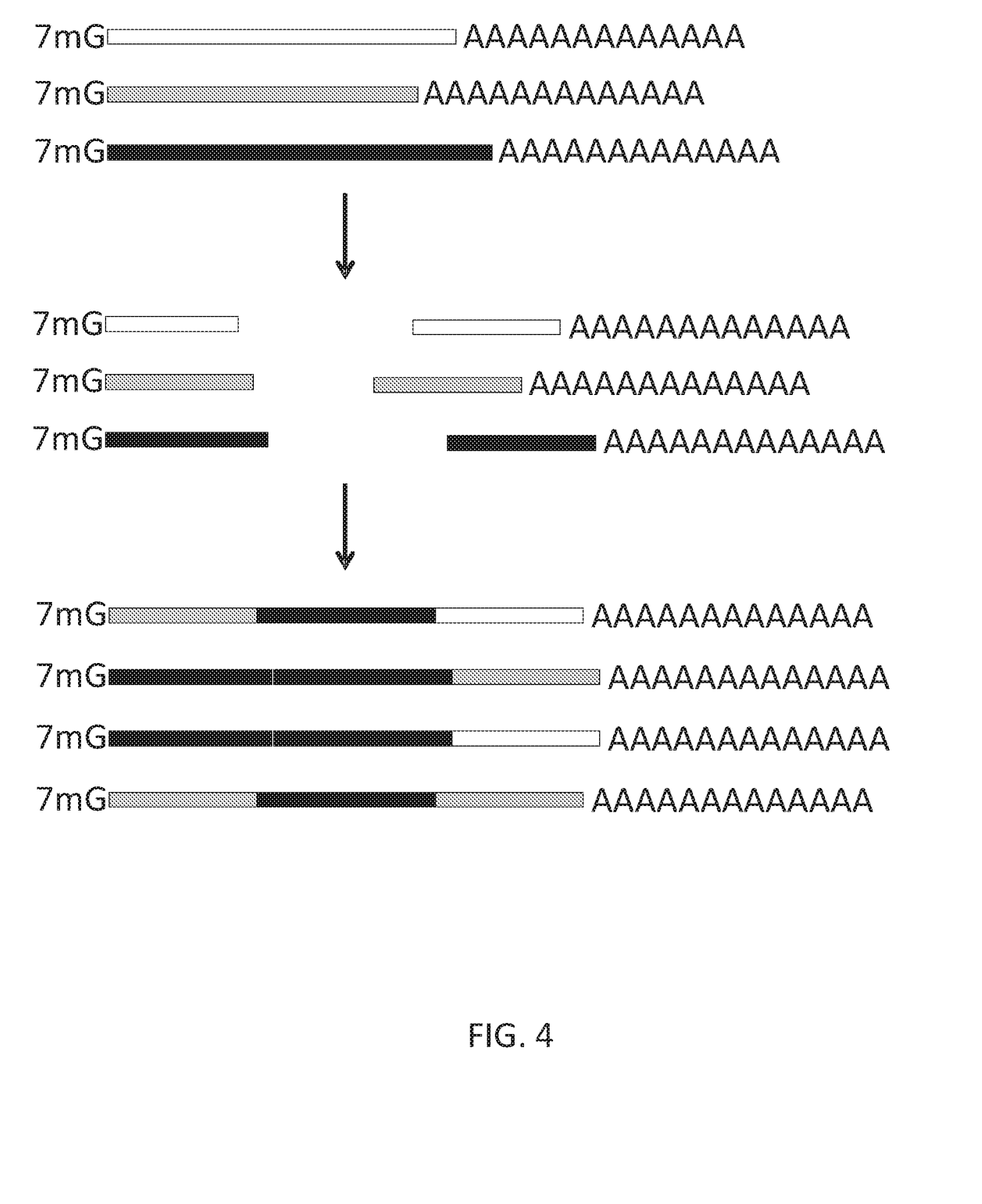
FIG. 4 shows construction of a combinatorial library of UTRs with a reporter as described herein. The method involves identifying mRNAs likely to be stable in liver, synthesizing UTRs of these mRNA sequences, and building combinatorial library of UTRs flanking a reporter gene, e.g., enhanced Green Fluorescent Protein (eGFP) or any other suitable reporter gene.

A combinatorial library of constructs (including, for example, a reporter gene) can be used to evaluate the effects of heterologous 5' and 3' UTRs on mRNA stability (FIG. 4). Such a library can be constructed, for example, by identifying mRNAs likely to be stable in a specific tissue, e.g., liver, synthesizing UTRs of these mRNA sequences, and building combinatorial library of UTRs flanking a reporter gene, e.g., enhanced Green Fluorescent Protein (eGFP) or any other suitable reporter gene.

Identification of mRNAs Stable in Liver

Figure 5:
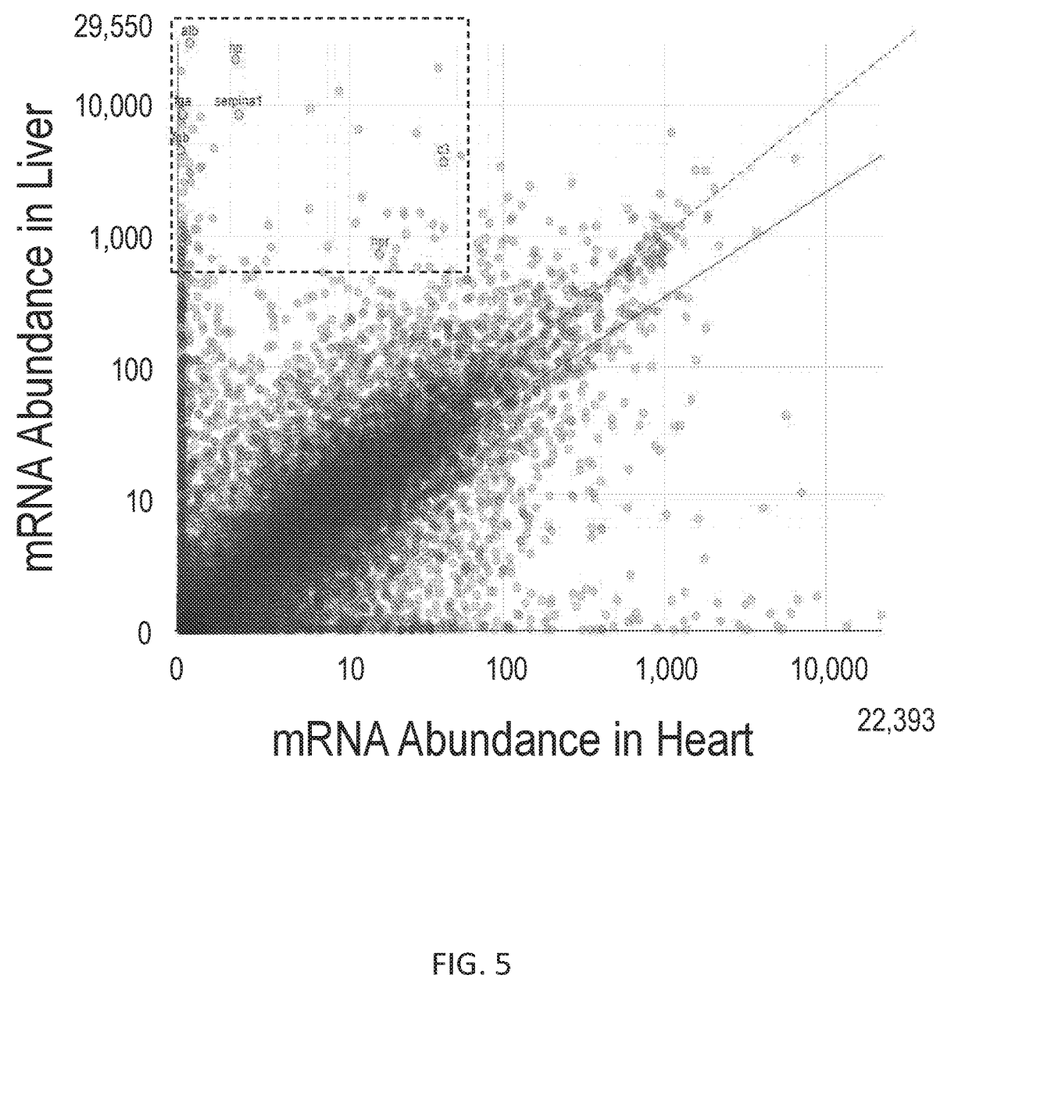
FIG. 5 shows selection of UTRs based on liver abundance (contrasted with abundance in other tissues, e.g., heart). mRNAs for the genes Haptoglobin (HP), Haptoglobin-Related Protein (HPR), Albumin (ALB), Complement Component 3 (C3), Alpha-1-antitrypsin (SERPINA1), Alpha-1-antichymotrypsin (SERPINA3), Fibrinogen Alpha Chain (FGA), and Fibrinogen Beta Chain (FGB) are naturally highly abundant in liver as compared with their prevalence in heart.

UTRs were selected based on liver abundance and stability measurements. As shown in FIG. 5 (inset), mRNAs for the genes Haptoglobin (HP), Haptoglobin-Related Protein (HPR), Albumin (ALB), Complement Component 3 (C3 Alpha-1-antitrypsin (SERPINA1 Alpha-1-antichymotrypsin (SERPINA3), Fibrinogen Alpha Chain (FGA), and Fibrinogen Beta Chain (FGB) are naturally highly abundant in liver as compared with their prevalence in heart.

Synthesis of UTRs

5' and 3' UTRs of each of HP, HPR, ALB, C3, SERPINA1, SERPINA3, FGA, and FGB genes were obtained via PCR and then sequenced by methods known in the art. The 5' UTRs of these genes are shown in Table 1.

TABLE 1

| Gene | SEQ ID NO | 5' UTR Sequence |
|---|---|---|
| HP | 1 | GGGAGAUGCCCCACAGCACUGCCCUUCCAGAGGCAAG ACCAACCAAG |
| FGB | 2 | GGGAGAUAUAUAUAGGAUUGAAGAUCUCUCAGUUAAG UCUACAUGAAAAGG |
| HPR | 3 | GGGACUGCCCUUCCAGAGGCAAGACCAACCAAG |
| ALB | 4 | GGGAGUAUAUUAGUGCUAAUUUCCCUCCGUUUGUCCU AGCUUUUCUCUUCUGUCAACCCCACA |
| C3 | 5 | GGGAGAUAAAAAGCCAGCUCCAGCAGGCGCUGCUCAC UCCUCCCCAUCCUCUCCCUCUGUCCCUCUGUCCCUCU GACCCUGCACUGUCCCAGCACC |
| FGA | 6 | GGGAGCAAUCCUUUCUUUCAGCUGGAGUGCUCCUCA GGAGCCAGCCCCACCCUUAGAAAAG |

TABLE 1-continued

| Gene | SEQ ID NO | 5' UTR Sequence |
|---|---|---|
| SERPINA1 | 7 | GGGAUUCAUGAAAAUCCACUACUCCAGACAGACGGCU UUGGAAUCCACCAGCUACAUCCAGCUCCCUGAGGCAG AGUUGAGA |
| Col1A | 8 | GGGGUGUCCCAUAGUGUUUCCAAACUUGGAAAGGGC GGGGGAGGGCGGGAGGAUGCGGAGGGCGGAGGUAU GCAGACAACGAGUCAGAGUUUCCCCUUGAAAGCCUCA AAAGUGUCCACGUCCUCAAAAAGAAUGGAACCAAUUU AAGAAGCCAGCCCCGUGGCCACGUCCCUUCCCCCAUU CGCUCCCUCCUCUGCGCCCCCGCAGGCUCCUCCCAG CUGUGGCUGCCCGGGCCCCCAGCCCCAGCCCUCCCA UUGGUGGAGGCCCUUUUGGAGGCACCCUAGGGCCAG GGAAACUUUUGCCGUAUAAAUAGGGCAGAUCCGGGCU UUAUUAUUUUAGCACCACGGCAGCAGGAGGUUUCGGC UAAGUUGGAGGUACUGGCCACGACUGCAUGCCCGCG CCCGCCAGGUGAUACCUCCGCCGGUGACCCAGGGGC UCUGCGACACAAGGAGUCUGCAUGUCUAAGUGCUAGA C |
| Col6A | 9 | GGGGCUUACUCGGCGCCCGCGCCUCGGGCCGUCGGG AGCGGAGCCUCCUCGGGACCAGGACUUCAGGGCCAC AGGUGCUGCCAAG |
| SERPINA3 | 10 | GGGACAAUGACUCCUUUCGGUAAGUGCAGUGGAAGC UGUACACUGCCCAGGCAAAGCGUCCGGGCAGCGUAG GCGGGCGACUCAGAUCCCAGCCAGUGGACUUAGCCC CUGUUUGCUCCUCCGAUAACUGGGGUGACCUUGGUU AAUAUUCACCAGCAGCCUCCCCCGUUGCCCCUCUGGA UCCACUGCUUAAAUACGGACGAGGACAGGGCCCUGUC UCCUCAGCUUCAGGCACCACCACUGACCUGGGACAGU GAAUCGACA |
| Engi-neered | 11 | GGGAAAUAAGAGAGAAAAGAAGAGUAAGAAGAAAUAUA AGAGCCACC |

Construction of Combinatorial Library of UTRs Flanking a Reporter Gene

Eleven 5' UTRs were used: eight from HP, FGB, HPR, ALB, C3, FGA, SERPINA1, and SERPINA3, (SEQ ID NOS: 1-7 and 10), which are derived from natural mRNAs in human liver tissue; two from collagens Col1A and Col6A SEQ ID NOS:9 and 10), which were among the most stable mRNAs in a study performed in a human fibroblast cell line (the only cell line in which global mRNA stabilities have been tested-showing a half-life of ~40-50 hours for each (Schwanhausser, B. et al., Nature, 473:337-42, 2011); and an engineered, synthetic 5' UTR (SEQ ID NO:11; Mandal, P. & Rossi, D., Nat. Protoc., 8:568-82, 2013).

Twelve 3'UTRs were used: eight from HP, FGB, HPR, ALB, C3, FGA, SERPINA1, SERPINA3, two from collagens (Col1A and Col6A), a synthetic 3' UTR (Mandal, P. & Rossi, D., Nat. Protoc., 8:568-82, 2013), and one from a long non-coding RNA (lncRNA), which is known to be stable and shown to stabilize other messages without depending on a poly-A tail.

eGFP, a fluorescent protein, was used as a reporter, and the eGFP ORF was used in all constructs to test 5' and 3' UTRs. eGFP was used because it can be easily measured by fluorescence read-out. Other suitable reporters, such as, for example, adiponectin and Factor VII, for example, are known in the art and may also be used.

If any of the tested UTRs, i.e., from HP, FGB, HPR, ALB, C3, FGA, SERPINA1 and SERPINA3 genes, for example, display greater stability and protein synthesis than the UTRs from collagen (Col1A and Col6A) and engineered UTRs, these UTRs may be functionally linked to a gene of interest, such as therapeutic gene, to test stability and synthesis of the gene of interest in, for example, liver, as compared with that in, for example, non-liver tissues. Alternatively, stability and synthesis may be tested in any other organ, tissue or cell system, including but not limited to stem cells or lymphocytes in vitro.

All 132 possible combinations of the eleven 5' UTRs and twelve 3' UTRs, plus eGFP reporter gene, were synthesized using natural nucleotides or modRNAs (which contain non-natural nucleotides, e.g., $N^1$-methyl-pseudouridine 5' triphosphate).

To test which UTRs perform best, eGFP mRNAs and eGFP modRNAs may be synthesized with variable UTR sequences as a pool, mRNAs or modRNAs transfected individually into primary hepatocytes, and eGFP production assessed at time points after transfection.

Generation of Plasmid DNA

Plasmids containing the sequences for the UTR library were synthesized and cloned into an in vitro transcription plasmid (DNA018). All 23 UTRs (eleven 5' UTRs and twelve 3' UTRs) and the reporter ORF were synthesized and combinatorially cloned into DNA018. Synthesis was performed using Gibson cloning, and constructs were inserted into the plasmid template using BsaI, thus, the components were free of BsaI cloning sites.

Generation of In Vitro Translated RNAs

Plasmids were pooled by 3' UTR, generating 12 pools, each containing 11 plasmids with identical 3' UTRs and differing 5' UTRs. Each pool was then linearized with EcoRI, producing single-stranded template. mRNAs and modRNAs were transcribed from each pool with T7 polymerase, using all natural nucleotides or nucleotides containing $N^1$-methyl-pseudouridine 5' triphosphate, respectively. mRNAs and modRNAs were capped during the in vitro transcription reaction using the anti-reverse cap analogue (ARCA). In vitro translated RNAs were then purified using methods known in the art.

The method of modRNA generation may result in several nucleotides being added to each end of the mRNA. At the 5' end of each message, there may be found GGG. This is imposed by the T7 promoter being used for transcription. At the 3' end of each message, there may be found GAAUU following the poly-A tail. This may exist because EcoRI is used for template linearization.

Testing Protein Synthesis modRNAs were generated from the construct of interest through in vitro transcription using just a single plasmid as template, and eGFP synthesis was measured following transfection in primary hepatocytes, using a fluorescence read-out.

EXAMPLE

Figure 6:
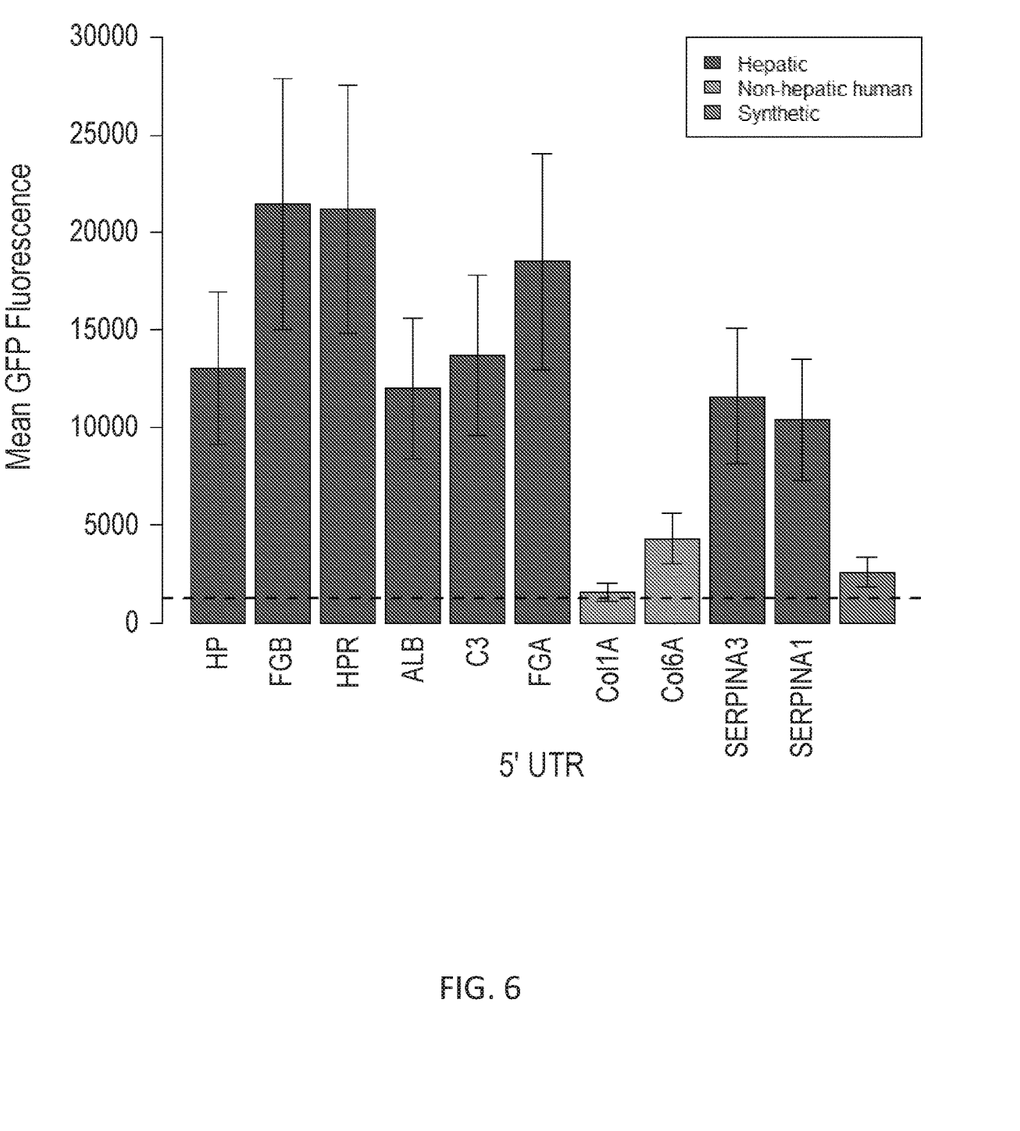
FIG. 6 shows that modified RNAs having hepatocyte 5' UTRs out-performed modified RNAs having synthetic or non-hepatic UTRs. modRNAs having hepatocyte 5' UTRs derived from HP, FGB, HPR, ALB, C3, FGA, SERPINA1 and SERPINA3 genes produced more eGFP than synthetic and non-hepatic (Col1A and Col6A) UTRs in primary hepatocytes after transfection.

FIG. 6 shows that modRNAs having hepatocyte 5' UTRs derived from HP, FGB, HPR, ALB, C3, FGA, SERPINA1 and SERPINA3 genes produced more eGFP than synthetic and non-hepatic (Col1A and Col6A) UTRs in primary hepatocytes after transfection. These results suggest that hepatocyte 5' UTRs are liver-specific for RNA stability, protein synthesis, or both. All messages were transfected in triplicate in primary hepatocytes. Standard deviation is ~30% on all samples.

Figure 7:
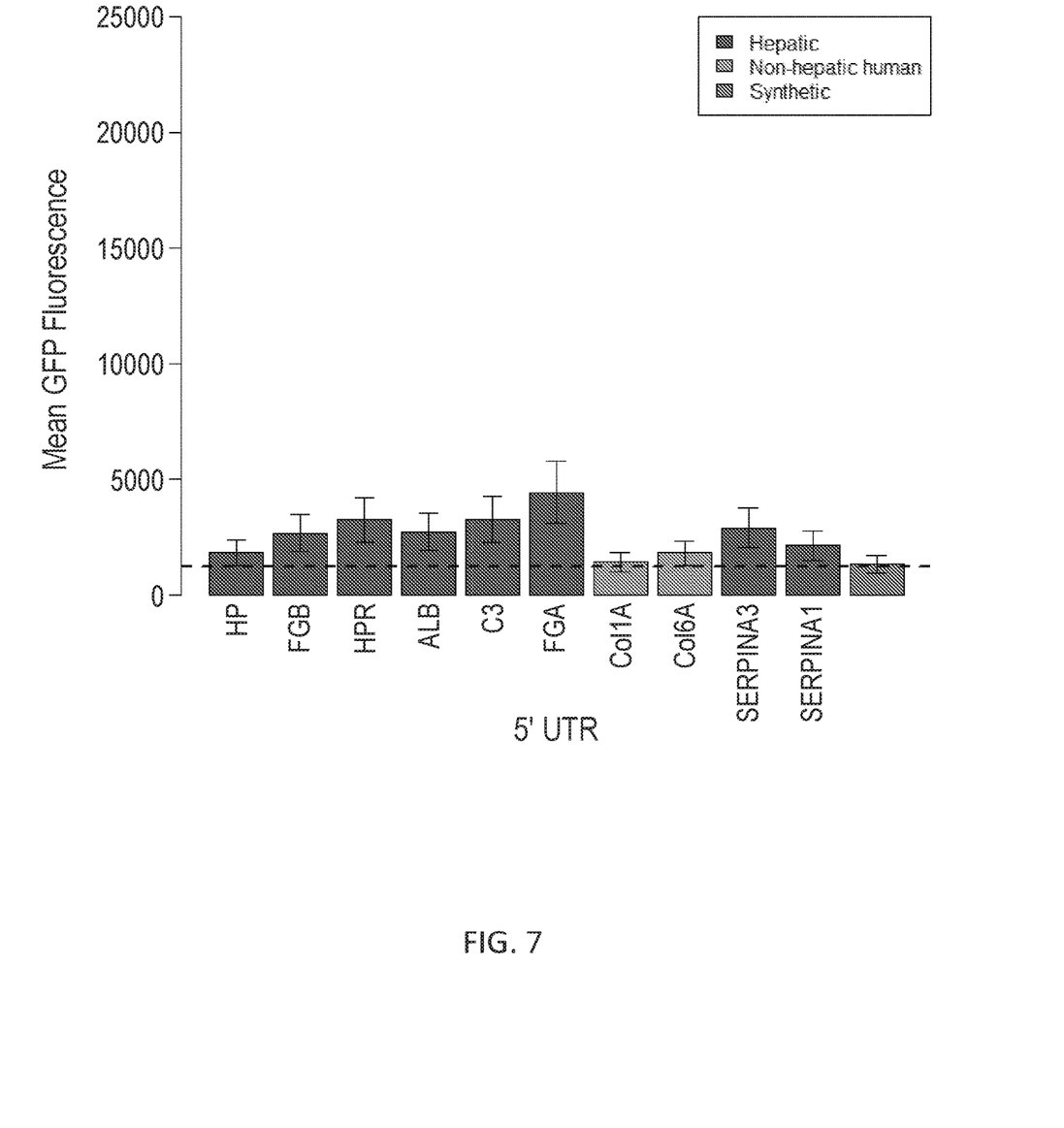
FIG. 7 shows that modified mRNA out-performed native mRNAs for all constructs. eGFP synthesis was reduced for all mRNAs containing only natural nucleotides, as compared with modRNAs (compare with FIG. 6).

On the other hand, mRNAs containing only natural nucleotides produced less eGFP than modRNAs, for all constructs tested. As shown in FIG. 7, eGFP synthesis was reduced for all mRNAs containing only natural nucleotides, as compared with modRNAs (compare with FIG. 6). These results suggest that modified nucleotides increase mRNA stability and/or protein synthesis. Importantly, the liver-specific effect of hepatocyte 5' UTRs persists because mRNAs containing only natural nucleotides and having hepatocyte 5' UTRs still out-performed those having synthetic and non-hepatic (Col1A and Col6A) UTRs. All messages were transfected in triplicate in primary hepatocytes. Standard deviation is ~30% on all samples.

Thus, in addition to rendering modRNAs nonimmunogenic, the present disclosure shows the surprising results that the modified nucleoside pseudouridine can also increase RNA stability and/or protein synthesis.

The 5' and 3' UTRs may be functionally linked to an ORF, which ORF may be a therapeutic gene encoding protein for preventing or treating liver conditions such as, for example, acute hepatitis, chronic hepatitis, liver cirrhosis, cirrhosis, fatty liver, or liver cancer, and the like. Additional liver diseases or conditions that can be treated or prevented by the compositions and methods described herein include, for example, any liver-associated enzyme deficiency such as, for example, glycogen storage disease, progressive familial intrahepatic cholestasis 1 (PFIC1), progressive familial intrahepatic cholestasis 2 (PFIC2), progressive familial intrahepatic cholestasis 3 (PFIC3), adenylosuccinate lyase deficiency (ASLD), citrullinemia, arginase-1 deficiency, primary hyperoxaluria type 1 (PH1), ornithine transcarbamylase deficiency (OTCD), homocystinuria, pheylketonuria, glycogen storage disease type IV (GSDIV), galactose-1-phosphate uridylyltransferase deficiency (galactosemia, e.g., type I (GALTI), type II (GALTII) or type 3 (GALTIII)), long chain 3-hydroxyacyl-CoA dehydrogenase deficiency (LCHADD), 3-methylcrotonyl-CoA carboxylase deficiency (MCCC1 deficiency), methylmalonic aciduria (MMA), MMA and homocystinuria type C (MMACHC), thrombotic thrombocytopenic purpura (TTP), hyperornithinemia-hyperammonemia-homocitrullinuria syndrome (HHH), complement component 2 deficiency (C2D), F2, protein S deficiency (caused by allelic variants of PROS1), alpha-1 antitrypsin deficiency (A1AT), glutaric academia 1 (GA-1), glutaric academia 2 (GA-2), cystinosis (CTNS), tyrosinemia, tyrosinemia type 3 (cause by allelic variants of HPD), D-bifunctional protein deficiency (DBP), Fanconi-Bickel syndrome (FBS), pseudoxanthoma elasticum (PXE), primary biliary cirrhosis, Pompe disease, glycerol kinase deficiency (GKD), proprionic acidemia (PA) and Crigler-Najjar syndrome (CN, e.g., CN1). Protein expressed from mRNAs comprising one or more heterologous UTRs can be provided for treating liver condition (hepatitis C) such as interferon alpha, TNF-related apoptosis-inducing ligand, vascular adhesion protein 1, hepatocyte growth factor, and the like may be provided.

Molecular targets for replacement therapies that can include heterologous UTRs as described herein, include, for example, gene products from the group consisting of: interferon alpha, TNF-related apoptosis-inducing ligand, vascular adhesion protein 1, hepatocyte growth factor, G6PC, ABCB11, ABCB4, ASL1, ASS, Arg1, AGXT, OTC, CBS, PAH, GBE, GALE, HADH, MCCC1, MMA, ADAMTS13, SLC25A15, C2, F2, PROS1, SERPINA1, GALT1, ETFA, GCDH, CTNS, FAH, TAT, HPD, HSD17b4, SLC2A2, GALC, ABCC6, AHSG, PDC-E2, GAA, ATP8B1, MMACHC, GK, PCCA, PCCB and UGT1A1.

In addition to liver, the present disclosure may be applied to other tissues and cells in which increased stability and/or translation efficiency of therapeutic mRNAs is desired. For example, to engineer lymphocytic cells or stem cells for therapeutic purposes, stability of therapeutic mRNAs after delivery may be increased by generating mRNAs, including, for example, modRNAs, having UTRs, derived from mRNAs that are naturally abundant in lymphocytic cells or stem cells, linked to one or more therapeutic ORFs.

The present disclosure differs from previous mRNA therapy efforts, which have relied on standard UTR sequences that are not tissue-specific, and give consistent but lower levels of protein expression. Thus, the present disclosure provides a significant advantage over the art by enabling mRNA therapies for treatment of chronic conditions that require sustained, high-level protein synthesis.

All references cited in this specification are herein incorporated by reference as though each reference was specifically and individually indicated to be incorporated by reference. The citation of any reference is for its disclosure prior to the filing date and should not be construed as an admission that the present disclosure is not entitled to antedate such reference by virtue of prior disclosure. It will be understood that each of the elements described above, or two or more together may also find a useful application in other types of methods differing from the type described above. Without further analysis, the foregoing will so fully reveal the gist of the present disclosure that others can, by applying current knowledge, readily adapt it for various applications without omitting features that, from the standpoint of prior art, fairly constitute essential characteristics of the generic or specific aspects of this disclosure set forth in the appended claims. The foregoing embodiments are presented by way of example only; the scope of the present disclosure is to be limited only by the following claims.

What is claimed is:

1. A method of expressing a protein in a liver tissue, comprising providing an mRNA to said liver tissue, wherein the mRNA comprises an open reading frame (ORF) that encodes said protein, flanked by a heterologous 5' untranslated region (UTR) and/or a heterologous 3' UTR, wherein the 5' UTR and/or the 3' UTR are derived from a gene selected from the group consisting of Haptoglobin (HP), Haptoglobin-Related Protein (HPR), Complement Component 3 (C3), Alpha-1-antitrypsin (SERPINA1), Alpha-1-antichymotrypsin (SERPINA3), Fibrinogen Alpha Chain (FGA), and Fibrinogen Beta Chain (FGB).

2. The method of claim 1, wherein the mRNA comprises at least one modified or non-naturally occurring nucleotide.

3. The method of claim 2, wherein the at least one modified or non-naturally occurring nucleotide comprises at least one backbone modification, sugar modification or base modification.

4. The method of claim 3, wherein the at least one modified or non-naturally occurring nucleotide comprises at least one base modification.

5. The method of claim 4, wherein the at least one base modification is selected from the group consisting of: 2-amino-6-chloropurine riboside 5' triphosphate, 2-aminoadenosine 5' triphosphate, 2-thiocytidine 5' triphosphate, 2-thiouridine 5' triphosphate, 4-thiouridine 5' triphosphate, 5-aminoallylcytidine 5' triphosphate, 5-aminoallyluridine 5' triphosphate, 5-bromocytidine 5' triphosphate, 5-bromouridine 5' triphosphate, 5-iodocytidine 5' triphosphate, 5-iodouridine 5' triphosphate, 5-methylcytidine 5' triphosphate, 5-methyluridine 5' triphosphate, 6-azacytidine 5' triphosphate, 6-azauridine 5' triphosphate, 6-chloropurine riboside 5'-triphosphate, 7-deazaadenosine 5' triphosphate, 7-deazaguanosine 5' triphosphate, 8-azaadenosine 5' triphosphate, 8-azidoadenosine 5' triphosphate, benzimidazole riboside 5' triphosphate, $N^1$-methyladenosine 5' triphosphate, $N^1$-methylguanosine 5' triphosphate, $N^6$-methyladenosine 5' triphosphate, $O^6$-methylguanosine 5' triphosphate, $N^1$-methyl-pseudouridine 5' triphosphate, puromycin 5'-triphosphate and xanthosine 5' triphosphate.

6. The method of claim 5, wherein the at least one modified or non-naturally occurring nucleotide is $N^1$-methyl-pseudouridine 5-triphosphate.

7. The method of claim 1, wherein the mRNA comprises a heterologous 5' UTR derived from a gene selected from the group consisting of: HP, FGB, HPR, C3, FGA, SERPINA1 and SERPINA3.

8. The method of claim 1, wherein the 5' UTR comprises a nucleotide sequence selected from the group consisting of: SEQ ID NOS:1-3, 5-7, and 10.

9. The method of claim 1, wherein the ORF is therapeutic gene.

10. The method of claim 9, wherein the therapeutic gene is selected from the group consisting of: interferon alpha, TNF related apoptosis-inducing ligand, vascular adhesion protein 1, hepatocyte growth factor, G6PC, ABCB11, ABCB4, ASL1, ASS, Arg1, AGXT, OTC, CBS, PAH, GBE, GALE, HADH, MCCC1, MMA, ADAMTS13, SLC25A15, C2, F2, PROS1, SERPINA1, GALT1, ETFA, GCDH, CTNS, FAH, TAT, HPD, HSD17b4, SLC2A2, GALC, ABCC6, AHSG, PDC-E2, GAA, ATP8B1, MMACHC, GK, PCCA, PCCB and UGT1A1.

11. The method of claim 1, wherein the mRNA comprises a heterologous 5' UTR derived from the FGB gene.

12. The method of claim 1, wherein the 5' UTR comprises the nucleotide sequence set forth in SEQ ID NO:2.

* * * * *

SEQUENCE LISTING

<160> NUMBER OF SEQ ID NOS: 11

<210> SEQ ID NO 1
<211> LENGTH: 47
<212> TYPE: RNA
<213> ORGANISM: Homo sapiens

<400> SEQUENCE: 1
gggagaugcc ccacagcacu gcccuuccag aggcaagacc aaccaag      47

<210> SEQ ID NO 2
<211> LENGTH: 51
<212> TYPE: RNA
<213> ORGANISM: Homo sapiens

<400> SEQUENCE: 2
gggagauaua uauaggauug aagaucucuc aguuaagucu acaugaaaag g      51

```
<210> SEQ ID NO 3
<211> LENGTH: 33
<212> TYPE: RNA
<213> ORGANISM: Homo sapiens

<400> SEQUENCE: 3
gggacugccc uuccagaggc aagaccaacc aag                           33

<210> SEQ ID NO 4
<211> LENGTH: 63
<212> TYPE: RNA
<213> ORGANISM: Homo sapiens

<400> SEQUENCE: 4
gggaguauau uagugcuaau uucccuccgu uuguccuagc uuuucucuuc ugcaaccccc   60
aca                                                            63

<210> SEQ ID NO 5
<211> LENGTH: 96
<212> TYPE: RNA
<213> ORGANISM: Homo sapiens

<400> SEQUENCE: 5
gggagauaaa aagccagcuc cagcaggcgc ugcucacucc uccccauccu cucccucugu   60
cccucugucc cucugacccu gcacugsccc agcacc                        96

<210> SEQ ID NO 6
<211> LENGTH: 61
<212> TYPE: RNA
<213> ORGANISM: Homo sapiens

<400> SEQUENCE: 6
gggagcaauc cuuucuuuca gcuggagugc uccucaggag ccagccccac ccuuagaaaa   60
g                                                              61

<210> SEQ ID NO 7
<211> LENGTH: 82
<212> TYPE: RNA
<213> ORGANISM: Homo sapiens

<400> SEQUENCE: 7
gggauucaug aaaauccacu acuccagaca gacggcuuug gaauccacca gcuacaucca   60
gcucccugag gcagaguuga ga                                       82

<210> SEQ ID NO 8
<211> LENGTH: 474
<212> TYPE: RNA
<213> ORGANISM: Homo sapiens

<400> SEQUENCE: 8
gggguguccc auaguguuuc caaacuugga aagggcgggg gagggcggga ggaugcggag   60
ggcggaggua ugcagacaac gagucagagu uuccccuuga agccucaaa agugccacg   120 uccucaaaaa gaauggaacc aauuuaagaa gccagccccg uggccacguc ccuucccca   180 uucgcucccu ccucugcgcc cccgcaggcu cucccagcu guggcugccc gggccccag   240 ccccagcccu cccauuggug gaggcccuuu uggaggcacc cuaggccag ggaaacuuuu   300 gccguauaaa uagggcagau ccgggcuuua uuauuuuagc accacggcag caggaggguu  360
```

```
cggcuaaguu ggagguacug gccacgacug caugcccgcg cccgccaggu gauaccuccg        420
ccggugaccc aggggcucug cgacacaagg agucugcaug ucuaagugcu agac             474

<210> SEQ ID NO 9
<211> LENGTH: 85
<212> TYPE: RNA
<213> ORGANISM: Homo sapiens

<400> SEQUENCE: 9
ggggcuuacu cggcgcccgc gccucgggcc gucgggagcg gagccuccuc gggaccagga        60
cuucagggcc acaggugcug ccaag                                             85

<210> SEQ ID NO 10
<211> LENGTH: 264
<212> TYPE: RNA
<213> ORGANISM: Homo sapiens

<400> SEQUENCE: 10
gggacaauga cuccuuucgg uaagugcagu ggaagcugua cacugcccag gcaaagcguc        60
cgggcagcgu aggcgggcga cucagauccc agccagugga cuuagcsccu guuugcuccu       120
ccgauaacug gggugaccuu gguuaauauu caccagcagc cuccccguu gccccucugg        180 auccacugcu uaaauacgga cgaggacagg gcccugucuc cucagcuuca ggcaccacca       240
cugaccuggg acagugaauc gaca                                             264

<210> SEQ ID NO 11
<211> LENGTH: 47
<212> TYPE: RNA
<213> ORGANISM: artificial
<220> FEATURE:
<223> OTHER INFORMATION: engineered 5' UTR

<400> SEQUENCE: 11
gggaaauaag agagaaaaga agaguaagaa gaaauauaag agccacc                     47
```

UNITED STATES PATENT AND TRADEMARK OFFICE
CERTIFICATE OF CORRECTION

PATENT NO. : 11,389,546 B2
APPLICATION NO. : 15/781827
DATED : July 19, 2022
INVENTOR(S) : Burkhardt et al.

It is certified that error appears in the above-identified patent and that said Letters Patent is hereby corrected as shown below:

In the Claims

<u>Column 18</u>
Claim 9, Line 66, delete "is" and insert -- is a --.

Signed and Sealed this
Eighteenth Day of October, 2022

Katherine Kelly Vidal
*Director of the United States Patent and Trademark Office*